United States Patent [19]
Cutie et al.

[11] Patent Number: 4,854,700
[45] Date of Patent: Aug. 8, 1989

[54] COLUMN HOLDER FOR ON-COLUMN PHOTOMETRIC DETECTION

[75] Inventors: Sergio S. Cutie; Martin A. Langhorst; Stewart P. Wood, all of Midland, Mich.

[73] Assignee: The Dow Chemical Company, Midland, Mich.

[21] Appl. No.: 207,699

[22] Filed: Jun. 15, 1988

[51] Int. Cl.$^4$ .............................................. G01N 30/74
[52] U.S. Cl. .................... 356/72; 73/61.1 C; 356/410; 356/244
[58] Field of Search .............. 356/72, 244, 246, 410, 356/411, 440; 73/61.1 C; 250/576

[56] References Cited

U.S. PATENT DOCUMENTS

| | | | |
|---|---|---|---|
| 4,008,397 | 2/1977 | Zdrodowski | 250/373 |
| 4,375,163 | 3/1983 | Yang | 73/61.1 C |
| 4,601,582 | 7/1986 | Casey, Jr. | 356/414 |
| 4,605,305 | 8/1986 | Lenoir et al. | 356/246 |

OTHER PUBLICATIONS

Larry A. Spino, Soon M. Han, Daniel W, Armstrong, Albert R. Parrott, "Inexpensive, Low-Dead Volume Flow Cells for Microcolumn LC", Journal of Liquid Chromatography, vol. 10 (8 & 9), 1987, pp. 1603–1611.
Robert Tijssen, Jaap Bos, M. Emile von Kreveld, "Hydrodynamic Chromatography of Macromolecules in Open Microcapillary Tubes", Analytical Chemistry, vol. 58, No. 14, Dec. 1986, pp. 3036–3044.

*Primary Examiner*—Vincent P. McGraw
*Attorney, Agent, or Firm*—Timothy S. Stevens

[57] ABSTRACT

A column holder for on-column photometric dectection capillary liquid chromatography incorporating a body and a pair of straight edges attached to the body. The straight edges can be conveniently made from a razor blade. The body has two passageways through it that are transverse and intersecting. The first passageway is dimensioned so that a capillary column can be slipped into it or removed from it by hand. The other passageway is for the passage of a light beam from a liquid chromatography photometric detector. The straight edges are slightly separated to form an optical slit in front of the capillary column and are securely clamped to the body of the column holder. A capillary column can be removed from the column holder and be replaced with another capillary column without damaging it and without the necessity of repositioning the slit.

2 Claims, 1 Drawing Sheet

COLUMN HOLDER FOR ON-COLUMN PHOTOMETRIC DETECTION

FIELD OF THE INVENTION

The invention is in the field of liquid chromatography and more specifically is in the field of capillary liquid chromatography.

BACKGROUND OF THE INVENTION

Liquid chromatography is an important branch of analytical chemistry. Recent advances to increase the efficiency and speed of separations performed using liquid chromatography have centered on reducing particle size of the chromatographic packing, reducing column diameter and using open tubular columns analogous to capillary gas chromatography. Open tubular capillary liquid chromatography is a technique that potentially can yield much better efficiency and speed than conventional technology. In order to exploit the advantages of open tubular capillary liquid chromatography, specialized instrumentation and techniques must be used. Yang, U.S. Pat. No. 4,375,163, disclosed on-column detection liquid chromatography with externally coated fused silica capillary columns wherein a segment of the external coating is removed at the end of the column to expose the underlying fused silica and this segment is then positioned in the optical path of a photometric detector. An optical slit is aligned with the longitudinal axis of the column and its use significantly increases the signal to noise ratio associated with detection because the light passes only through the center of the column and is not defracted by the sides of the column. Yang's advance was a major one and much research has been published by others who use this approach. Most workers, including Yang, report using the Jasco Incorporated UVIDEC flow cell holder, adapting it for on-column detection according to Yang, by threading the capillary column on the flow cell holder and then clamping the column in place in front of the slit of the flow cell holder. A problem with the Jasco Incorporated flow cell holder so adapted for on-column detection arises because the column must be bent through four right angles to fit in place on the holder and can break where the external coating has been removed, i.e., the column is quite fragile where the coating has been removed. Another problem with the Jasco Incorporated flow cell holder is that each time a column is fitted thereto, the column must be carefully aligned in front of the slit and then clamped in place without disturbing the alignment.

Spino et al., *Journal of Liquid Chromatography*, 1987, pages 1603–1611, disclosed a flow cell having a body shaped to be held in a photometric detector. A section of externally coated fused silica capillary tubing with a segment of the coating removed is laid on the body transverse to a passageway through the body. A pair of straight edges (razor blades) are carefully positioned along the segment to form an optical slit. The tube and razor blades are permanently held to the body with glue. The flow cell of Spino was not used for on-column detection and rather the end of the column was connected to the section of tubing glued to the body. If the flow cell of Spino had been used for on-column detection (thus converting it into a column holder), it would have solved the above-mentioned problem of breakage due to the bending of the column but each time a new column was used the old one would have to be demounted from the body, probably breaking or otherwise damaging it, and the slit would have to be carefully reset.

It would be an advance in the art of on-column detection liquid chromatography if a column holder were developed that allowed a capillary column to be easily changed without damaging it and without the necessity of repositioning the slit.

SUMMARY OF THE INVENTION

The present invention is a column holder for on-column photometric detection capillary liquid chromatography that allows a capillary column to be easily changed without damaging it and without the necessity of repositioning the optical slit. The present invention incorporates a body and a pair of straight edges attached to the body, the straight edges being separated to form an optical slit. The body has a first passageway through it so that a capillary liquid chromatography column can be inserted through it and can also be retracted, by hand. The body also has a second passageway through it which is transverse and intersecting with the first passageway so that light can be shown into the second passageway, can pass through a column inserted through the first passageway and then can pass out of the second passageway on its way to a photodetector. The straight edges are separated to form an optical slit which is positioned in or adjacent the second passageway and adjacent the first passageway so that the longitudinal axis of the optical slit is aligned with the longitudinal axis of the first passageway.

DETAILED DESCRIPTION OF THE INVENTION

Figure 1:
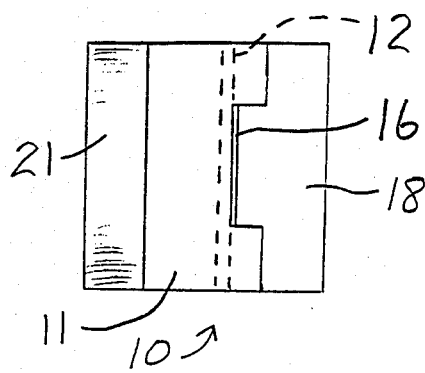
FIG. 1 is a side view of a column holder embodiment according to the present invention showing a body having a passageway therethrough so that a capillary column can be placed therein.

Referring now to FIGS. 1–4, therein is shown side, top, back and front views of a column holder 10 according to the present invention. The column holder 10 has a body 11. The body 11 has a first passageway 12 therethrough. The first passageway 12 is dimensioned so that a liquid chromatographic capillary column can be inserted therethrough and can be retracted by hand, and yet remain therein by friction between the passageway 12 and such a column. The body 11 also has a second passageway 13 therethrough. The second passageway has an inlet end 14 and an outlet end 15. The second passageway 13 is transverse and intersecting with the first passageway 12 so that light can be shown into the inlet end 14 of the second passageway 13, can pass through a capillary column inserted through the first passageway 12 and then pass out of the outlet end 15 of the second passageway 13. A pair of straight edges 16 and 17 are shown clamped to the body 11 by a clamp portion 18 of the body 11 and screws 19. The straight edges 16 and 17 are shown being slightly separated to form an optical slit 20 which is positioned in the second passageway 13 and adjacent the first passageway 12. The optical slit 20 has a longitudinal axis along the optical slit which is aligned to be along the longitudinal axis of the first passageway 12. Preferably, the optical slit of the present invention is immediately adjacent the first passageway for optimum optical efficiency. The optical slit can be positioned at the end of the second passageway rather than in it, i.e., adjacent the second passageway.

The preferred way to align the slit 20 is to insert an externally coated fused silica column, having a segment of the external coating removed at the end of the column to expose the underlying fused silica, into the passageway 12 so that this segment also is positioned in the second passageway 13. Then, by loosening the screws 19, the straight edges 16 and 17 are manually moved to position the slit 20 directly in line of the bore of the inserted column with respect to the longitudinal axis of the second passageway 13. This is best done under a microscope and especially for columns that have small internal diameters. The screws 19 are then retightened to clamp the straight edges 16 and 17 to the body 11. The alignment of the slit 20 is then confirmed and if not disturbed by tightening the screws 19, remains properly aligned even if the column is removed from the passageway 12 and another is inserted that has essentially the same internal and external diameter. Generally, the slit 20 should be somewhat thinner than the internal diameter of the column for optimum signal to noise ratio of detection just as was the case with prior column holders. The diameter of the first passageway 12 must be larger than the outside diameter of a column to be inserted thereinto. However, the clearance between the outside of the column and the first passageway 12 should be minimal while still maintaining a slip fit between the column and the first passageway 12. Friction between the column and the first passageway 12 will normally keep the uncoated segment of the column within the second passageway 13 once it is positioned there. The straight edges 16 and 17 can conveniently be made from single edge razor blade segments.

Figure 2:
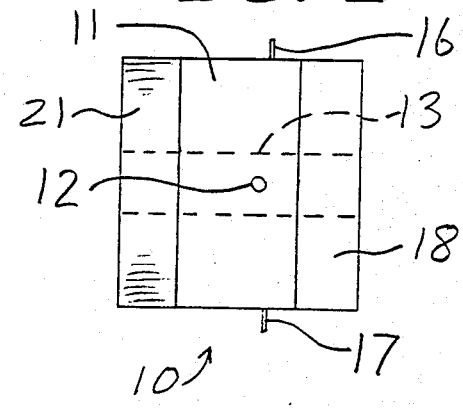
FIG. 2 is a top view of the column holder of FIG. 1, showing another passageway therethrough so that a beam of light can be passed therethrough.
Figure 3:
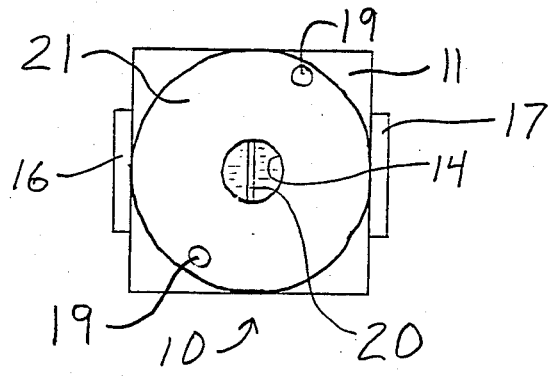
FIG. 3 is a rear view of the column holder of FIG. 1, showing a perforated disk screwed to the body of the holder, the perforated disk adapted to mount the column holder to a liquid chromatography photometric detector.
Figure 4:
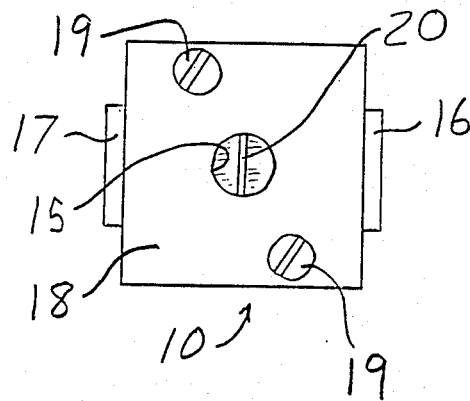
FIG. 4 is a front view of the column holder of FIG. 1 showing the clamp portion and screw heads thereof.

FIGS. 1-3 also show a perforated disk 21 attached to the body 11 by the screws 19. The disk 21 is designed to be held by the cell clamp of a Kratos Analytical liquid chromatography photometric detector such as the Kratos Spectroflow 773 variable wavelength detector. Other brands and types of photometric detectors may, of course, require different means of attaching the column holder of the present invention to the detector. The perforated disk 21 is preferably made of stainless steel but can be made of other metals or other materials such as a plastic. The body 11 is preferably made of Teflon ® brand plastic but can be made of other materials such as another plastic or a metal. It is easier to drill the first passageway 12 when the body 11 is Teflon ® brand plastic than when it is stainless steel. The clamp portion 18 is also preferably made of Teflon ® brand plastic but can be made of other materials.

Figure 5:
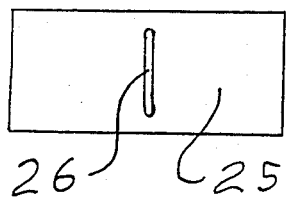
FIG. 5 is a front view of an alternative pair of unitized straight edges according to the present invention, adapted to be used in the column holder of FIGS. 1–4.

FIG. 5 shows an alternative pair of straight edges according to the present invention in the form of a unitized pair of straight edges 25 defining a slit 26. The slit 26 can be formed by laser machining techniques. The slit 26 is not adjustable as to width but is easier to position in the column holder 10. Preferably, the unitized pair of straight edges 25 is made from a strip of stainless steel but other materials can be used. It should be understood that the straight edges can be micrometer mounted to the body of the column holder of the present invention and with precision machining techniques, the straight edges of the present invention could be formed integrally with the body.

EXAMPLE

A column holder 10 is manufactured having a Teflon ® brand plastic body 11 and clamp portion 18, a stainless steel perforated disk 21 and razor blade segment straight edges 16 and 17. The straight edges are aligned as discussed above using a microscope to form an optical slit between the knife edges of the razor blade segments for a 10 micrometer internal diameter polyimide coated fused silica column. The perforated disk 21 has an outside diameter dimensioned to fit the cell holder of a Kratos Spectroflow 773 photometric detector. The flow cell of the detector is removed and the column holder 10 is installed in its place. A liquid chromatographic column is prepared as a three and a quarter meter long length of 10 micrometer internal diameter polyimide externally coated fused silica capillary tubing cut from a stock roll of this tubing. The inside of the column is not coated with a chromatographically active phase or filled with a chromatographically active packing because the column is to be used for hydrodynamic chromatography in this example. However, packed or coated capillary columns can be used, in the scientific sense, with the column holder of the present invention. Such users should additionally refer to U.S. Pat. No. 4,375,163 to Yang.

The end of the column is inserted through the passageway 12 of the holder 10. The polyimide coating is removed from a half-inch long segment of the column a distance a quarter of a meter from the end of the column. The uncoated segment of the column is positioned approximately in the center of the passageway 12. The end of the column is inserted into a one-ounce waste collection bottle. The inlet end of the column is connected to a micro injection valve. A constant pressure liquid chromatography pump is connected to the injection valve and is set at a pressure that pumps eluent at 5.6 nanoliters per minute through the injection valve, through the column and then into the waste collection bottle. The eluent is water containing two millimolar sodium dihydrogen phosphate, 0.5 grams per liter of sodium dodecyl sulfate and two grams per liter of Brij 35 surfactant. A strip chart recorder is connected to the detector to record chromatograms from the system. The detector is set at 210 nanometers, for the fastest response time and at 0.0002 absorbance units full scale output of the strip chart recorder. A sample is prepared containing 1000 parts per million by weight (ppm) of potassium dichromate and 5000 ppm sulfonated polystyrene in water. The sulfonated polystyrene has a weight average molecular weight of about 195,000. A 100 picoliter injection of the sample is made and a chromatogram is recorded on the strip chart recorder showing two peaks, one for the sulfonated polystyrene and a later one for the lower molecular weight dichromate.

Another column is prepared as above. The original column is removed from the column holder and the new column installed therein and plumbed to the res of the system. Another injection of the sample is made and a chromatogram is recorded on the strip chart recorder showing two peaks, one for the sulfonated polystyrene and a later one for the lower molecular weight dichromate.

What is claimed is:

1. A column holder for on-column photometric detection capillary liquid chromatography, comprising:
   (a) a body, the body having a first passageway therethrough, so that a capillary liquid chromatography column can be inserted through the first passageway and can be retracted therefrom by hand, the first passageway having a longitudinal axis, the body also having a second passageway therethrough, the second passageway having an inlet end and an outlet end, the second passageway being transverse and intersecting with the first passageway so that light can be shown into the inlet end of the second passageway, can pass through such a column inserted through the first passageway and then can pass out of the outlet end of the second passageway;
   (b) a pair of straight edges, the straight edges attached to the body, the straight edges being separated to form an optical slit between the pair of straight edges, the optical slit positioned in or adjacent the second passageway and adjacent the first passageway, the optical slit having a longitudinal axis along the optical slit, the longitudinal axis along the optical slit being aligned along the longitudinal axis of the first passageway.

2. The column holder of claim 1, wherein the straight edges are attached to the body by a clamp so that the straight edges can be adjusted as to position and then held in place relative to the body.

* * * * *